(12) United States Patent
Sajja

(10) Patent No.: US 10,736,726 B2
(45) Date of Patent: Aug. 11, 2020

(54) MECHANICAL PROSTHETIC HEART VALVE ASSEMBLY FOR THE PROVISION OF SURFACE ANTICOAGULATION THEREON

(71) Applicant: Lokeswara Rao Sajja, Hyderabad (IN)

(72) Inventor: Lokeswara Rao Sajja, Hyderabad (IN)

(*) Notice: Subject to any disclaimer, the term of this patent is extended or adjusted under 35 U.S.C. 154(b) by 60 days.

(21) Appl. No.: 15/646,713

(22) Filed: Jul. 11, 2017

(65) Prior Publication Data

US 2019/0015187 A1    Jan. 17, 2019

(51) Int. Cl.
| | | |
|---|---|---|
| *A61F 2/24* | (2006.01) | |
| *A61F 2/00* | (2006.01) | |
| *A61N 1/05* | (2006.01) | |
| A61F 2/48 | (2006.01) | |
| A61N 1/32 | (2006.01) | |

(52) U.S. Cl.
CPC .......... *A61F 2/0077* (2013.01); *A61F 2/2403* (2013.01); *A61F 2/2409* (2013.01); *A61N 1/056* (2013.01); *A61F 2002/0091* (2015.04); *A61F 2002/482* (2013.01); *A61F 2250/0001* (2013.01); *A61N 1/32* (2013.01)

(58) Field of Classification Search
CPC .................. A61F 2/2403; A61F 2/0077; A61F 2250/0001
See application file for complete search history.

(56) References Cited

U.S. PATENT DOCUMENTS

| | | |
|---|---|---|
| 3,609,768 A | 5/1971 | Ayres |
| 2006/0089709 A1* | 4/2006 | Helmus ..................... A61F 2/91 623/1.44 |
| 2006/0106451 A1 | 5/2006 | Busiashvili |
| 2007/0123765 A1* | 5/2007 | Hetke ................ A61B 5/04001 600/378 |
| 2010/0087918 A1* | 4/2010 | Vesely .................. A61F 2/2403 623/2.27 |

* cited by examiner

*Primary Examiner* — Christopher D. Prone
(74) *Attorney, Agent, or Firm* — Fresh IP PLC; Aubrey Y Chen

(57) ABSTRACT

A mechanical prosthetic heart valve assembly for the provision of surface anticoagulation by generating an electrostatic field of a plurality of negatively charged ions thereon, acting as neo-endothelium on the mechanical prosthetic heart valve, referred as Surface Anticoagulation by Electrical Neo-endothelialization (SAEN). The mechanical prosthetic heart valve assembly comprises a mechanical prosthetic heart valve housing; a pair of mechanical prosthetic heart valve discs; a mechanical prosthetic heart valve sewing ring; an implantable pulse generator serving as a source of electricity for generating the electrostatic field of the plurality of negatively charged ions thereon the surface of the mechanical prosthetic heart valve; a pulse generator bipolar lead connected to the outer surface of the mechanical prosthetic heart valve housing, using an electrode; and a polytetrafluoroethylene (PTFE) graft sutured to margins of a fenestration on the mechanical prosthetic heart valve sewing ring.

7 Claims, 5 Drawing Sheets

MECHANICAL PROSTHETIC HEART VALVE ASSEMBLY FOR THE PROVISION OF SURFACE ANTICOAGULATION THEREON

This non-provisional application claims priority to Indian Patent Application No. 201741016200, filed on May 8, 2017, which is incorporated herein by reference in its entirety.

FIELD OF THE INVENTION

The present invention generally relates to the field of prosthetic heart valve. Particularly, the invention relates to a mechanical prosthetic heart valve assembly for the provision of surface anticoagulation thereon. More particularly, the invention provides a mechanical prosthetic heart valve assembly for the provision of surface anticoagulation thereon by generating an electrostatic field of a plurality of negatively charged ions thereon the surface of the housing and discs of the mechanical prosthetic heart valve.

BACKGROUND OF THE INVENTION

Medical science and technological development associated therewith have witnessed a phenomenal advancement in recent years. In spite of tremendous efforts, the anticoagulation related problems like bleeding or thrombosis are considered to be some of the challenging problems that medical professionals and technologist have been attempting to solve.

According to various prior art disclosures, oral anticoagulation in patients who receive mechanical heart valve implantation is associated with problems of valve thrombosis if anticoagulation is suboptimal or bleeding complications if prothombin time (PT) and international normalization ratios (INR) are high. Prior art literature illustrates a number of approaches for such problems. Mechanical prosthetic heart valve implantation in humans requires anticoagulation postoperatively to prevent thromboembolic events. The traditional method disclosed by the prior art of oral anticoagulation is using warfarin and it requires periodic blood testing to check prothrombin time (PT) and International normalized ratio (INR) to achieve optimal therapeutic levels of PT, INR to prevent thrombosis or bleeding. Also, patients who are on anticoagulation have restricted physical activities, avoiding contact sports that limit lifestyle to the young patients and in female patients going through pregnancy.

In addition, prior art also discloses that the implanted mechanical prosthetic heart valves are thrombogenic because of the accumulation of more positively charged ions at the site of implantation. Prior art also discloses that healthy human arteries, veins or other blood and tissue interfaces carry a negative surface charge of approximately 0.3 volt which is necessary to prevent coagulation of blood. However prior arts do not disclose the utilization of such surface charge to prevent adherence of platelets and adsorption of fibrinogen as of now.

Thus, in the light of the above mentioned background art, it is evident that, there is a need for a mechanical prosthetic heart valve assembly for the provision of surface anticoagulation, which could generate an electrostatic field of negatively charged ions thereon the surface of the housing and discs of the mechanical prosthetic heart valve. There is also a need for a mechanical prosthetic heart valve assembly for the provision of surface anticoagulation, wherein the generated electrostatic field of negatively charged ions thereon the surface of the housing and discs of the mechanical prosthetic heart valve could potentially acts as a neo-endothelium to prevent adherence of activated platelets and adsorption of fibrinogen on to the surface of the prosthetic heart valve. A mechanical prosthetic heart valve assembly for the provision of surface anticoagulation thereon is desired.

OBJECTIVES OF THE INVENTION

In accordance with the present invention, the primary objective is to provide a mechanical prosthetic heart valve assembly for the provision of surface anticoagulation thereon.

Another objective of the present invention is to provide a mechanical prosthetic heart valve assembly for the provision of surface anticoagulation by generating an electrostatic field of a plurality of negatively charged ions thereon the surface of the housing and discs of the mechanical prosthetic heart valve.

Another objective of the present invention is to provide a mechanical prosthetic heart valve assembly for the provision of surface anticoagulation, wherein the generated electrostatic field of negatively charged ions thereon the surface of the housing and discs of the mechanical prosthetic heart valve could potentially act as a neo-endothelium to prevent adherence of activated platelets and adsorption of fibrinogen on to the surface of the housing and discs of the mechanical prosthetic heart valve.

SUMMARY OF THE INVENTION

Before the present methods, systems, and hardware enablement are described, it is to be understood that this invention in not limited to the particular systems, and methodologies described, as there can be multiple possible embodiments of the present invention which are not expressly illustrated in the present disclosure. It is also to be understood that the terminology used in the description is for the purpose of describing the particular versions or embodiments only, and is not intended to limit the scope of the present invention.

The present invention provides a mechanical prosthetic heart valve assembly for the provision of surface anticoagulation thereon.

In an embodiment of the invention a mechanical prosthetic heart valve assembly is provided with surface anticoagulation by generating an electrostatic field of a plurality of negatively charged ions thereon the surface of the housing and discs of the mechanical prosthetic heart valve.

In an embodiment of the invention a mechanical prosthetic heart valve assembly for the provision of surface anticoagulation is provided, wherein the generated electrostatic field of negatively charged ions thereon the surface of the housing and discs of the mechanical prosthetic heart valve could potentially act as a neo-endothelium to prevent adherence of activated platelets and adsorption of fibrinogen on to the surface of the mechanical prosthetic heart valve.

In an embodiment of the invention a mechanical prosthetic heart valve assembly (100) for the provision of surface anticoagulation is provided. The mechanical prosthetic heart valve assembly (100) disclosed herein provides surface anticoagulation by generating an electrostatic field of a plurality of negatively charged ions thereon the surface of the mechanical prosthetic heart valve, acting as an electrical neo-endothelium on the mechanical prosthetic heart valve. The mechanical prosthetic heart valve assembly (100) for the provision of surface anticoagulation comprises a mechanical prosthetic heart valve housing (102); a pair of mechanical prosthetic heart valve discs (104) attached to perimeter of the mechanical prosthetic heart valve housing (102) at two areas; a mechanical prosthetic heart valve sewing ring (106) encircling the mechanical prosthetic heart valve housing (102); an implantable pulse generator (108) serving as a source for electricity for generating the electrostatic field of the plurality of negatively charged ions thereon the surface of the mechanical prosthetic heart valve, a pulse generator bipolar lead (110) connected to the outer surface of the mechanical prosthetic heart valve housing (102), using an electrode (112) coupled to the tip of the pulse generator bipolar lead (110) connected on to the outer surface of the housing of the mechanical prosthetic heart valve (102); and a polytetrafluoroethylene (PTFE) graft (114) sutured to margins of a fenestration (116) created on the mechanical prosthetic heart valve sewing ring (106) to provide electrode (112) coupled to the tip of the pulse generator bipolar lead (110) with an access to the outer surface of the housing of the mechanical prosthetic heart valve (102).

The above said mechanical prosthetic heart valve assembly is provided with surface anticoagulation but the said principle of generation of electronegativity on the surface of implanted metallic devices may potentially be used for other applications where the prevention of platelet adhesion and fibrin adsorption is required.

BRIEF DESCRIPTION OF THE DRAWINGS

The foregoing summary, as well as the following detailed description of preferred embodiments including aspects and features of the invention, are better understood when read in conjunction with the appended drawings. The drawing is not necessarily to scale, emphasis instead generally being placed upon illustrating the principles of the invention. For the purpose of illustrating the invention, there is shown in the drawings exemplary constructions of the invention; however, the invention is not limited to the specific methods and system disclosed. In the drawings.

DETAILED DESCRIPTION OF THE INVENTION

Figure 1:
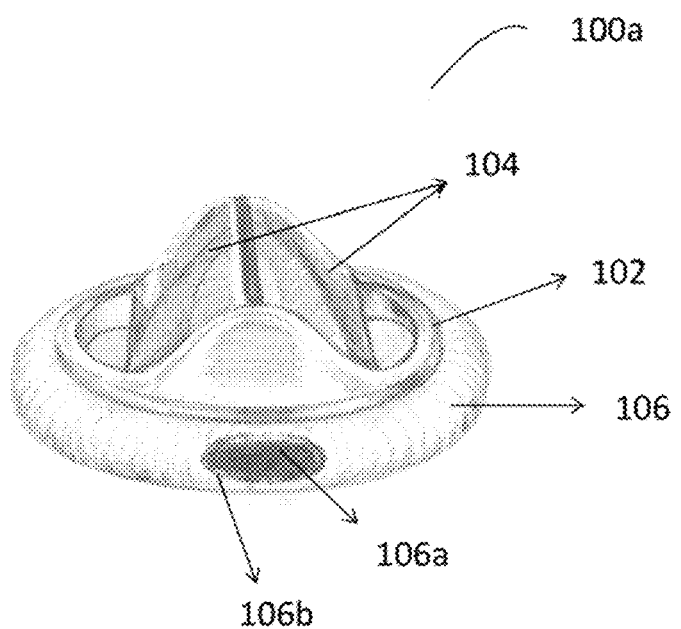
FIG. 1: illustrates a mechanical prosthetic heart valve sub-assembly comprising a mechanical prosthetic heart valve for the provision of surface anticoagulation without an implantable pulse generator, in accordance with one embodiment of the present invention.

Some embodiments of this invention, illustrating all its features, will now be discussed in detail.

Reference throughout this specification to "an embodiment", "another embodiment" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems or other elements or other structures or additional devices or additional sub-systems or additional elements or additional structures.

Unless otherwise defined, all technical and scientific terms used herein have the same meaning as commonly understood by one of ordinary skill in the art to which this invention belongs to. The system, methods, and examples provided herein are illustrative only and not intended to be limiting.

Embodiments of the present invention will be described below in detail with reference to the accompanying drawings.

The disclosed embodiments are merely exemplary of the invention, which may be embodied in various forms.

Glossary of Terms and Respective Definitions

Anticoagulation: An agent that is used to prevent the formation of blood clots.

Anticoagulants has various uses, some are used for the prevention or treatment of disorders characterized by abnormal blood clots and emboli.

Platelets: a small colorless disc-shaped cell fragment without a nucleus found in large numbers in blood and involved in clotting.

Fibrinogen: a soluble protein present in blood plasma, from which fibrin is produced by the action of the enzyme thrombin.

Platelet rich plasma: Platelet rich plasma (PRP) which is considered as an ideal autologous biological blood derived product, which contains high concentrations of platelets.

Prosthetic heart valve: Prosthetic heart valve is a surgical implant used to replace an abnormal heart valve.

Pacemaker: A medical device which uses electrical impulses, delivered by electrodes contracting the heart muscles, to regulate the beating of the heart.

PT, INR: The prothrombin time (PT) and international normalized ratio (INR) are assays evaluating the extrinsic pathway of coagulation. They are used to determine the clotting tendency of blood, in the measure of warfarin dosage.

Pyrolytic carbon: Pyrolytic carbon is a material similar to graphite used for making heart valves which is of Biocompatible, i.e. does not elicit any adverse reactions when implanted into human bodies, thromboresistant i.e. resists blood clotting, good durability, good wear resistance, good strength.

Scanning electron microscope: The scanning electron microscope (SEM) uses a focused beam of high-energy electrons to generate a variety of signals at the surface of solid specimens. The SEM is routinely used to generate highresolution images of shapes of objects (SEI) and to show spatial variations in chemical compositions.

The present invention provides a mechanical prosthetic heart valve assembly (100) for the provision of surface anticoagulation thereon.

In an embodiment of the present invention, the mechanical prosthetic heart valve assembly (100) for the provision of surface anticoagulation by generating an electrostatic field of a plurality of negatively charged ions thereon the surface of the housing and discs of the mechanical prosthetic heart valve, acting as an electrical neo-endothelium on the mechanical prosthetic heart valve, may be referred as Surface Anticoagulation by Electrical Neo-endothelialization (SAEN). The mechanical prosthetic heart valve assembly (100) for the provision of surface anticoagulation comprises of: a mechanical prosthetic heart valve housing (102); a pair of mechanical prosthetic heart valve discs (104) attached to the perimeter of the mechanical prosthetic heart valve housing (102) at two areas; a mechanical prosthetic heart valve sewing ring (106) encircling the mechanical prosthetic heart valve housing (102); an implantable pulse generator (108) serving as a source of electricity for generating the electrostatic field of the plurality of negatively charged ions thereon the surface of the mechanical prosthetic heart valve housing (102); a pulse generator bipolar lead (110) connected to the outer surface of the mechanical prosthetic heart valve housing (102), using an electrode (112) coupled to the tip of the pulse generator bipolar lead (110) connected on to the outer surface of the housing of the mechanical prosthetic heart valve (102); and a polytetrafluoroethylene (PTFE) graft (114) sutured to margins of a fenestration (116) created on the mechanical prosthetic heart valve sewing ring (106) to provide electrode (112) coupled to the tip of the pulse generator bipolar lead (110) with an access to the outer surface of the housing of the mechanical prosthetic heart valve (102).

Referring to FIG. 1 is a mechanical prosthetic heart valve sub-assembly comprising a mechanical prosthetic heart valve for the provision of surface anticoagulation without an implantable pulse generator, in accordance with one embodiment of the present invention.

In another embodiment of the present invention, the mechanical prosthetic heart valve sub-assembly (100a) for the provision of surface anticoagulation may comprises of the mechanical prosthetic heart valve housing (102). The mechanical prosthetic heart valve assembly (100) for the provision of surface anticoagulation may further comprises of the pair of mechanical prosthetic heart valve discs (104) are attached to the perimeter of the mechanical prosthetic heart valve housing (102) at two areas. The mechanical prosthetic heart valve sub-assembly (100a) for the provision of surface anticoagulation may further comprises of the mechanical prosthetic heart valve sewing ring (106) which may be encircling the mechanical prosthetic heart valve housing (102).

Figure 2:
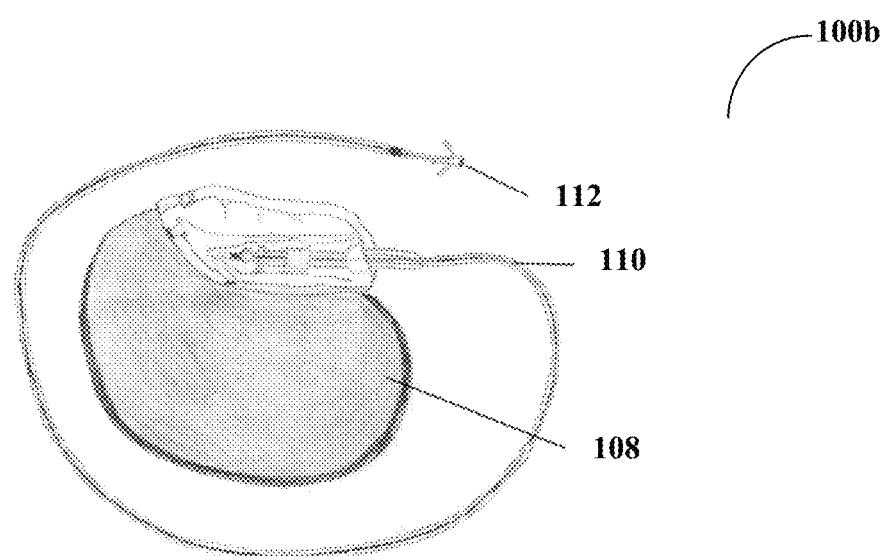
FIG. 2: illustrates a mechanical prosthetic heart valve sub-assembly comprising an implantable pulse generator with a pulse generator bipolar lead of a mechanical prosthetic heart valve assembly for the provision of electricity for generating the electrostatic field of the plurality of negatively charged ions for surface anticoagulation, in accordance with one embodiment of the present invention.

Referring to FIG. 2 is a mechanical prosthetic heart valve sub-assembly comprising an implantable pulse generator with a pulse generator bipolar lead of a pacemaker of the mechanical prosthetic heart valve assembly for the provision of electricity to the surface of the housing and discs of the heart valve, in accordance with one embodiment of the present invention.

In another embodiment of the present invention, the mechanical prosthetic heart valve sub-assembly (100b) for the provision of surface anticoagulation may comprises of the implantable pulse generator (108) which may be serving as the source for electricity for generating the electrostatic field of the plurality of negatively charged ions thereon the surface of the mechanical prosthetic heart valve. The mechanical prosthetic heart valve assembly (100) for the provision of surface anticoagulation may further comprises of the pulse generator bipolar lead (110) may be connected to the outer surface of the mechanical prosthetic heart valve housing (102), using the electrode (112) coupled to the tip of the pulse generator bipolar lead (110) connected on to the outer surface of the housing of the mechanical prosthetic heart valve (102).

Figure 3A:
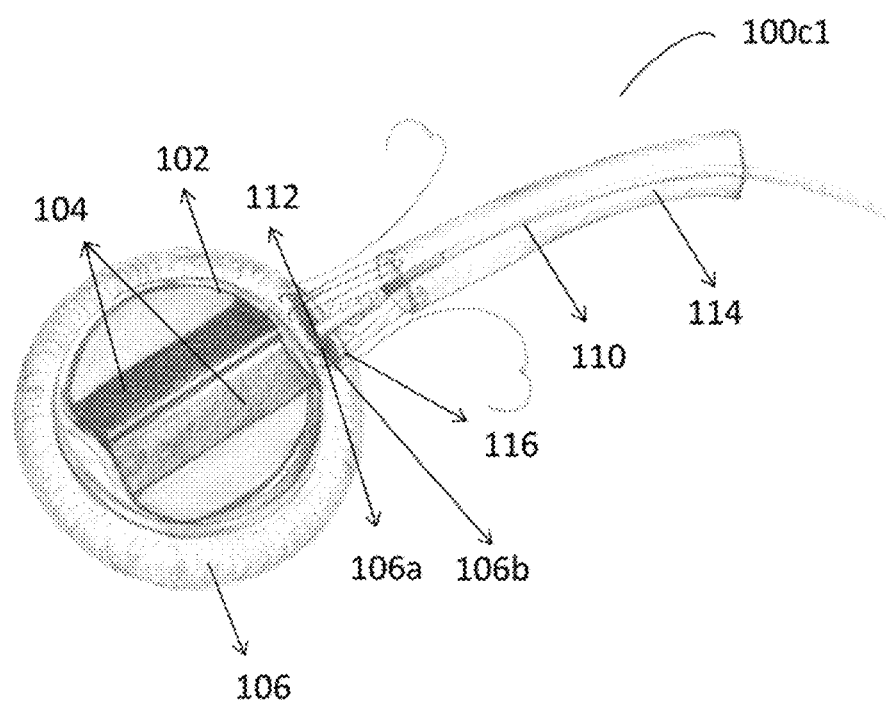
FIGS. 3A and 3B: illustrate a mechanical prosthetic heart valve sub-assembly comprising a fenestration created on a mechanical prosthetic heart valve sewing ring with an attached polytetrafluoroethylene (PTFE) graft on a mechanical prosthetic heart valve for securing the pulse generator bipolar lead (110) in place, in accordance with one embodiment of the present invention.
Figure 3B:
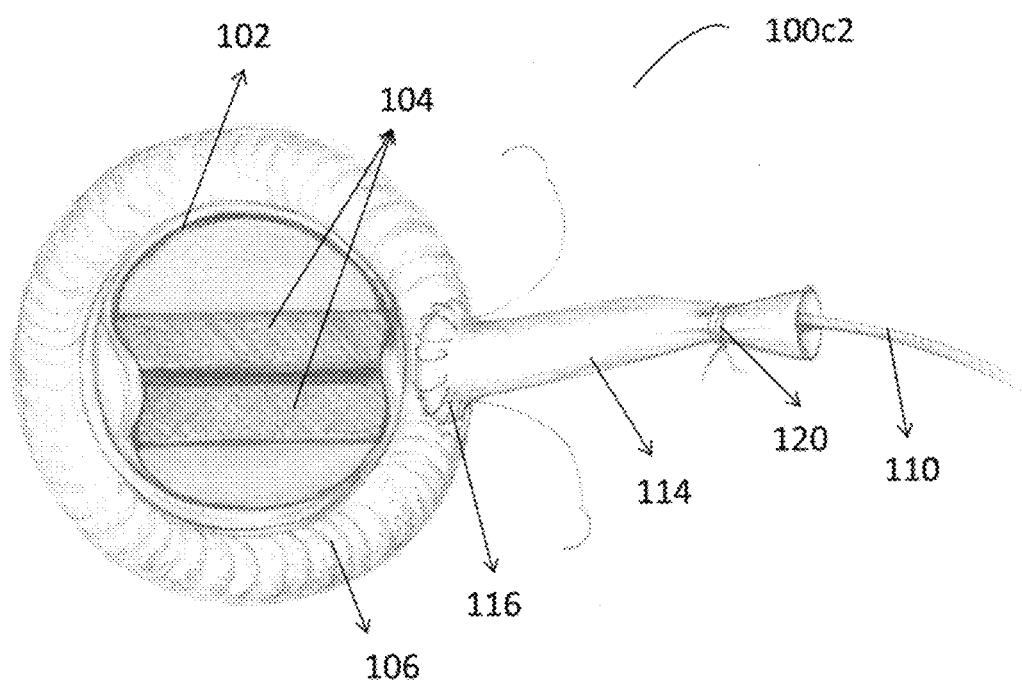

Referring to FIGS. 3A and 3B is a mechanical prosthetic heart valve sub-assembly comprising a fenestration created on a mechanical prosthetic heart valve sewing ring with an attached polytetrafluoroethylene (PTFE) graft on a mechanical prosthetic heart valve for the provision of securing the pulse generator bipolar lead (110) in place in accordance with one embodiment of the present invention.

In another embodiment of the present invention, the mechanical prosthetic heart valve sub-assembly (100c) for the provision of surface anticoagulation may comprises of the mechanical prosthetic heart valve housing (102). The mechanical prosthetic heart valve assembly (100) for the provision of surface anticoagulation may further comprises of the pair of mechanical prosthetic heart valve discs (104) which are attached to the perimeter of the mechanical prosthetic heart valve housing (102) at two areas. The mechanical prosthetic heart valve assembly (100) for the provision of surface anticoagulation may further comprises of the mechanical prosthetic heart valve sewing ring (106) which may be encircling the mechanical prosthetic heart valve housing (102).

In another embodiment of the present invention, the mechanical prosthetic heart valve assembly (100) for the provision of surface anticoagulation may comprises of the polytetrafluoroethylene (PTFE) graft (114) sutured to margins of the fenestration (116) created on the mechanical prosthetic heart valve sewing ring (106) to provide electrode (112) coupled to the tip of the pulse generator bipolar lead (110) with an access to the outer surface of the housing of mechanical prosthetic heart valve (102).

Figure 4:
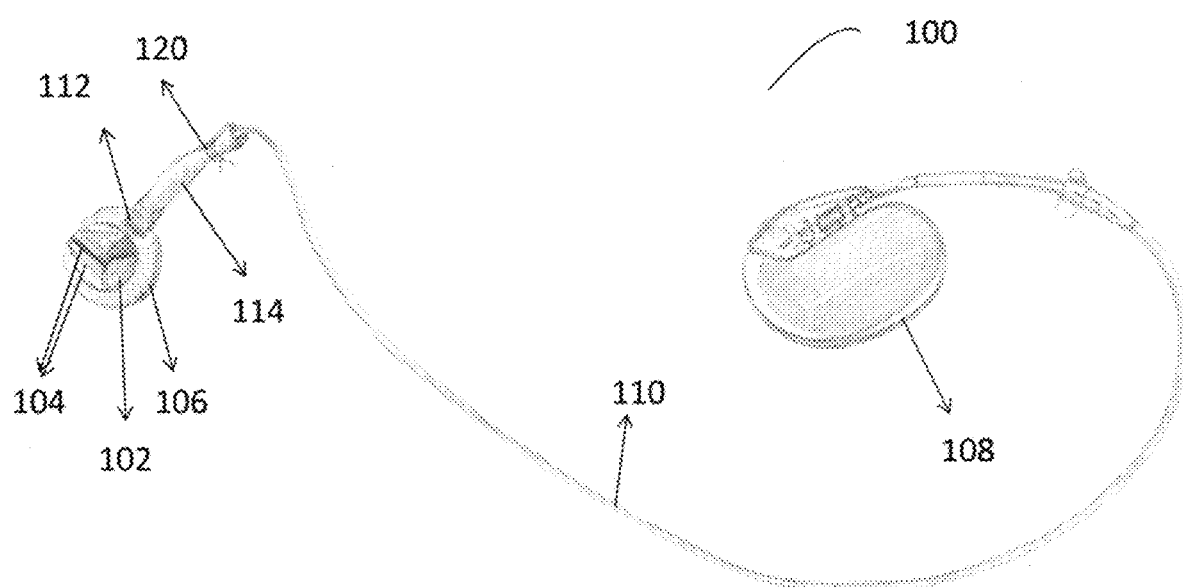
FIG. 4: illustrates a mechanical prosthetic heart valve assembly for the provision of surface anticoagulation with an implantable pulse generator, in accordance with one embodiment of the present invention.

Referring to FIG. 4 is a mechanical prosthetic heart valve assembly for the provision of surface anticoagulation with an implantable pulse generator, in accordance with one embodiment of the present invention.

In an exemplary embodiment of the present invention, the mechanical prosthetic heart valve assembly (100) may comprises of a mechanical prosthetic heart valve sub-assembly (100a); a mechanical prosthetic heart valve sub-assembly (100b); and a mechanical prosthetic heart valve sub-assembly (100c). The mechanical prosthetic heart valve assembly (100) may be a mechanical prosthetic heart valve assembly, which may be a bileaflet valve coated with pyrolytic carbon. The mechanical prosthetic heart valve assembly (100) for the provision of surface anticoagulation may comprises of the mechanical prosthetic heart valve housing (102). The mechanical prosthetic heart valve assembly (100) for the provision of surface anticoagulation may further comprises of the pair of mechanical prosthetic heart valve discs (104) which are attached to the perimeter of the mechanical prosthetic heart valve housing (102) at two areas. The mechanical prosthetic heart valve assembly (100) for the provision of surface anticoagulation may further comprises of the mechanical prosthetic heart valve sewing ring (106) which may be encircling the mechanical prosthetic heart valve housing (102).

In an exemplary embodiment of the present invention, the mechanical prosthetic heart valve assembly (100) for the provision of surface anticoagulation may comprises of the implantable pulse generator (108) which may be serving as the source of electricity for generating the electrostatic field of the plurality of negatively charged ions thereon the surface of the mechanical prosthetic heart valve. The generated electrostatic field of the plurality of negatively charged ions thereon the surface of the mechanical prosthetic heart valve acting as neo-endothelium which prevents adhesion of platelets and adsorption of fibrinogen on the surface of the mechanical prosthetic heart valve. The implantable pulse generator (108) serving as the source of electricity for generating the electrostatic field of the plurality of negatively charged ions thereon the surface of the mechanical prosthetic heart valve may be a pacemaker. Further, the pacemaker may be programmed to deliver and monitor pulse amplitude of 0.3V by using a programmer and telemetry. Traditionally, the pacemaker unit may deliver an electrical pulse with a proper intensity to a proper location to stimulate a human heart at a desired rate. The pulse generator of cardiac pacemaker may contain a power supply such as a battery. Impulses may be transmitted to the heart by means of the pulse generator bipolar lead (110).

In an exemplary embodiment of the present invention, the mechanical prosthetic heart valve assembly (100), the implantable pulse generator (108) may deliver an electrical pulse to the surface of the mechanical prosthetic heart valve assembly (100) at a pulse amplitude of 0.3V and at 70 impulses/min by means of pulse generator bipolar lead (110). The mechanical prosthetic heart valve assembly (100) for the provision of surface anticoagulation may further comprises of the pulse generator bipolar lead (110) may be connected to the outer surface of the mechanical prosthetic heart valve housing (102), using the electrode (112) coupled to the tip of the pulse generator bipolar lead (110) connected on to the outer surface of the housing of the mechanical prosthetic heart valve (102). The pulse generator bipolar lead (110) may contain two coils separated by an inner insulation and outer insulation to shield the pulse generator bipolar lead (110) from external environment.

In an exemplary embodiment of the present invention, the mechanical prosthetic heart valve assembly (100) for the provision of surface anticoagulation may comprises of the polytetrafluoroethylene (PTFE) graft (114) sutured to margins of the fenestration (116) created on the mechanical prosthetic heart valve sewing ring (106) to provide electrode (112) coupled to the tip of the pulse generator bipolar lead (110) with an access to the outer surface of the housing of the mechanical prosthetic heart valve (102). The polytetrafluoroethylene (PTFE) graft (114) sutured to margins of the fenestration (116) created on the mechanical prosthetic heart valve sewing ring (106) may be with the diameter of 6 mm. The fenestration (116) created on the mechanical prosthetic heart valve sewing ring (106) may be 5 mm of diameter. The electrode (112) may be coupled to the tip of the pulse generator bipolar lead (110) which may pass through the polytetrafluoroethylene (PTFE) graft (114) sutured to margins of the fenestration (116) created to secure the pulse generator bipolar lead (110) in place. This also may enable continuous contact of the electrode (112) which is coupled to the tip of the pulse generator bipolar lead (110) with the outer surface of the mechanical prosthetic heart valve housing (102). The pulse generator bipolar lead (110) may further be secured by tying (120) of a thread over the polytetrafluoroethylene (PTFE) graft (114).

In an exemplary embodiment of the present invention, the mechanical prosthetic heart valve assembly (100) for the provision of surface anticoagulation by generating the electrostatic field of a plurality of negatively charged ions thereon the surface of the mechanical prosthetic heart valve acting as neo-endothelium on the mechanical prosthetic heart valve is provided. An in vitro study was conducted by using the mechanical prosthetic heart valve assembly (100), which are a bileaflet valve coated with pyrolytic carbon and another mechanical prosthetic heart valve without electrical activation (control). The electrical activation was achieved from the power source of the implantable pulse generator (108) of a pacemaker. Both the mechanical prosthetic heart valves were immersed in platelet rich plasma (PRP) and were agitated with Envion shaker thermo stated at 35±2° C. for 30 min at 70±5 rpm. Scanning electron microscopy (SEM) of the each pair of mechanical prosthetic heart valve discs (104) of each of the mechanical prosthetic heart valves was done to assess the platelet adherence and fibrin deposition on both the valves. The mechanical prosthetic heart valve treated with electricity is fixed in 2% Glutaraldehyde and stored at 4° C. (overnight). Excess of fixative were washed with 0.1 M Cacodylate buffer three times with 10 mts interval and dehydrated in ascending order of Ethanol from 30-100% with 10 mts interval. The samples again dried in high vacuum (10-14 Torr) for complete removal of moisture. The valve mounted on Aluminum stub with double sided adhesive tape and coated with Gold thickness 600 Å in sputter coating unit E-1010 (Hitachi) to develop the conductivity. Scanned under 53400N (Hitachi) at 10 KV under high vacuum pictures were taken in 2K to 20K magnifications; area 20 µm to 2 µm. The SEM analysis showed there was no adherence of platelets and fibrinogen adsorption on the surface of the pair of mechanical prosthetic heart valve discs (104) of the electrically activated mechanical prosthetic heart valve while a significantly higher number of platelets adherent to the surface of the pair of valve discs of the mechanical prosthetic heart valve and adsorption fibrinogen on the pair of valve discs of mechanical prosthetic heart valve in the control group where the electrical activation is not done. Thereby, creating a permanent electrostatic field for 30 mins with a negative potential of 0.3 volts on the surface of the tested mechanical prosthetic heart valve the fibrin was not adsorbed and platelets were not adherent on to the surface of the mechanical prosthetic heart valve.

I claim:

1. A mechanical prosthetic heart valve assembly for provision of surface anticoagulation by generating an electrostatic field of a plurality of negatively charged ions on a surface of a mechanical prosthetic heart valve, acting as neo-endothelium on the mechanical prosthetic heart valve, the mechanical prosthetic heart valve for the provision of the surface anticoagulation comprising:

a mechanical prosthetic heart valve housing;

a pair of mechanical prosthetic heart valve discs attached to perimeter of the mechanical prosthetic heart valve housing at two areas;

a mechanical prosthetic heart valve sewing ring encircling the mechanical prosthetic heart valve housing for aiding implantation in the body;

an implantable pulse generator, serving as a source for electricity, generating the electrostatic field of the plurality of negatively charged ions on the surface of the mechanical prosthetic heart valve and the pair of mechanical prosthetic heart valve discs, wherein the implantable pulse generator delivers an electrical pulse to the surface of the mechanical prosthetic heart valve at a pulse amplitude of 0.3V and at 70 impulses/minute;

a pulse generator bipolar lead, wherein the pulse generator bipolar lead transfers electric current to the mechanical prosthetic heart valve housing by use of an electrode coupled to a tip of the pulse generator bipolar lead, wherein the electrode is connected on to an outer surface of the mechanical prosthetic heart valve housing, and wherein the electrode delivers the electric current on the surface of the mechanical prosthetic heart valve and enables generation of the electrostatic field; and a polytetrafluoroethylene (PTFE) graft sutured to the mechanical prosthetic heart valve sewing ring to provide the electrode coupled to the tip of the pulse generator bipolar lead with an access to the outer surface of the housing of the mechanical prosthetic heart valve.

2. The mechanical prosthetic heart valve assembly as claimed in claim 1, wherein the pulse generator through the electrode enables generation of the electrostatic field of the plurality of negatively charged ions on the surface of the mechanical prosthetic heart valve acting as neo-endothelium which prevents adhesion of platelets and adsorption of fibrinogen on the surface of the mechanical prosthetic heart valve discs.

3. The mechanical prosthetic heart valve assembly as claimed in claim 1, wherein said pulse generator is a part of a pacemaker.

4. The mechanical prosthetic heart valve assembly as claimed in claim 3, wherein the pacemaker is programmed to deliver and monitor pulse amplitude of 0.3V at 70 impulses per min by using a programmer and telemetry.

5. The mechanical prosthetic heart valve assembly as claimed in claim 1, wherein the electrode coupled to the tip of the pulse generator bipolar lead passes through the polytetrafluoroethylene (PTFE) graft sutured to secure the pulse generator bipolar lead in place and enables continuous contact of the electrode coupled to the tip of the pulse generator bipolar lead with the outer surface of the mechanical prosthetic heart valve housing.

6. The mechanical prosthetic heart valve assembly as claimed in claim 1, wherein the pulse generator bipolar lead is held in the polytetrafluoroethylene (PTFE) graft by tying of a thread over the polytetrafluoroethylene (PTFE) graft.

7. The mechanical prosthetic heart valve assembly as claimed in claim 1, wherein the polytetrafluoroethylene (PTFE) graft is defined by a diameter of 6 mm.

* * * * *